(12) United States Patent
Ikegami et al.

(10) Patent No.: US 6,395,681 B1
(45) Date of Patent: May 28, 2002

(54) FLUORENE COMPOUNDS

(75) Inventors: Seishi Ikegami; Takamichi Amako, both of Osaka (JP)

(73) Assignee: Appleton Papers Inc., Appleton, WI (US)

( * ) Notice: Subject to any disclaimer, the term of this patent is extended or adjusted under 35 U.S.C. 154(b) by 0 days.

(21) Appl. No.: 06/910,045

(22) Filed: Sep. 22, 1986

Related U.S. Application Data

(62) Division of application No. 06/603,265, filed on Apr. 23, 1984, now abandoned.

(30) Foreign Application Priority Data

Apr. 28, 1983 (JP) .............................. 58-74102

(51) Int. Cl.⁷ ........................ B41M 5/145; B41M 5/30
(52) U.S. Cl. ...................... 503/220; 427/151; 549/265
(58) Field of Search .................. 346/220; 549/265; 503/220; 427/151

(56) References Cited

U.S. PATENT DOCUMENTS 3,344,189 A * 9/1967 Davis .......................... 564/308
4,480,002 A * 10/1984 Asano et al. ............... 346/220

* cited by examiner

Primary Examiner—Bruce H. Hess
(74) Attorney, Agent, or Firm—Paul S. Phillips, Jr.; Benjamin Mieliuis

(57) ABSTRACT

Chromogenic compounds of colorless or lightly colored form are disclosed having the following structural formula:

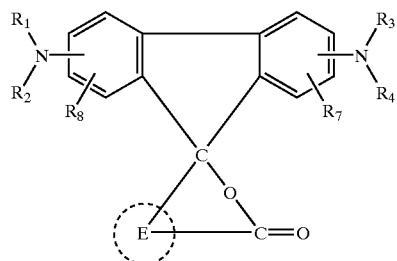

wherein E represents a six-membered aromatic or heterocyclic ring which may have an aromatic condensed ring and both the E ring and the condensed ring may be substituted.

Each of $R_1$, $R_2$, $R_3$ and $R_4$ independently represents hydrogen, alkyl of not more than 12 carbon atoms which is unsubstituted or substituted by halogen, hydroxyl, cyano or lower alkoxy or represents cycloalkyl, phenyl, benzyl, or phenyl or benzyl which is substituted by halogen, lower alkyl or lower alkoxy or $R_1$ and $R_2$ or $R_3$ and $R_4$ together with the nitrogen atom to which they are attached represent a 5- or 6-membered heterocyclic radical.

Each of $R_7$ and $R_8$ independently represents hydrogen, lower alkyl, lower alkoxy or halo.

The compounds of this invention are eligible for use in pressure-sensitive and heat-sensitive record materials and manifold marking systems.

11 Claims, No Drawings

FLUORENE COMPOUNDS

This is a division, of application Ser. No. 06/603,265, filed Apr. 23, 1984, now abandoned.

This invention relates to novel fluorene compounds, a process for their manufacture and recording materials comprising same.

More particularly, this invention pertains to novel chromogenic compounds which can give intense colors when they are contacted with an electron accepting co-reactant. Even more specifically, this invention relates to chromogenic compounds eligible for use in pressure-sensitive or heat-sensitive mark-forming record systems. Such systems are improved by use of these compounds. As used in mark-forming systems, marking in desired areas on support webs or sheets may be accomplished by effecting localized reactive contact between the chromogenic material and the electron accepting material on or in such a web or sheet, such material being brought thereto by transfer, or originally there in situ, the desired reactive contact forming colored images in the intended image-marking areas.

The chromogenic compounds of this invention have the following general formula:

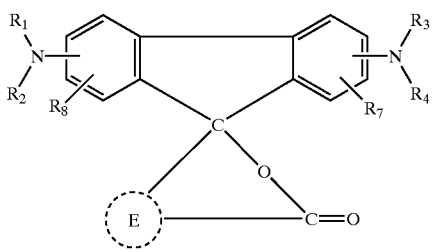

(1)

wherein E represents a six-membered aromatic or heterocyclic ring which may have an aromatic condensed ring and both the E ring and the condensed ring may be substituted.

Each of $R_1$, $R_2$, $R_3$ and R4 independently represents hydrogen, alkyl of not more than 12 carbon atoms which is unsubstituted or substituted by halogen, hydroxyl, cyano or lower alkoxy or represents cycloalkyl, phenyl, benzyl, or phenyl or benzyl which is substituted by halogen, lower alkyl or lower alkoxy or $R_1$ and $R_2$ or $R_3$ and $R_4$ together with the nitrogen atom to which they are attached represent a 5- or 6-membered heterocyclic radical.

Each of $R_7$ and $R_8$ independently represents hydrogen, lower alkyl, lower alkoxy or halo.

In the above definition of the radicals, lower alkyl or lower alkoxy denotes, as a rule, those groups which contain 1 to 5, preferably 1 to 3, carbon atoms.

Alkyl groups represented by $R_1$, $R_2$, $R_3$, $R_4$, $R_7$ or $R_8$ can be straight chain or branched. Cycloalkyl is, for example, cyclopentyl or preferably cyclohexyl.

If $R_1$ and $R_2$ or $R_3$ and $R_4$, together with the nitrogen atom to which they are attached, represent a heterocyclic radical, such a radical is, for example, pyrrolidino, piperidino, pipecolino, morpholino, thiomorpholino or piperazino.

U.S. Pat. Nos. 4,020,056; 4,022,771; 4,026,883; 4,107,428; and 4,119,776 disclose compounds having near infrared absorption and chromogenic properties. U.S. Pat. Nos. 3,344,189 and 3,413,071 and German Patent No. 2,145,027 disclose fluorene dye derivatives.

Of recording materials using colorless chromogenic compounds there are known a variety of forms such as pressure-sensitive copying paper, heat-sensitive recording paper, electrothermal recording paper, or the like, and with the advent of an informationalized era there is an increasing demand for these recording materials. Moreover, in recent years, computers have come into wide use for the rationalization of business, so that optical character readers are in use for feeding information to computers. Such an optical character reader is a device which can read information by the aid of the wavelengths in the near infrared region. Accordingly, in order to read information by means of an optical character reader it is essential that the information should be recorded with some material which is capable of absorbing the wavelengths in the near infrared region. However, the image obtained with the recording materials using the conventional chromogenic compounds had no absorption in the near infrared region, so that they had a shortcoming of being illegible by means of an optical character reader.

It has been discovered that recording materials comprising the fluorene compounds of this invention as the chromogenic material show remarkably good combination of color forming capability and absorption in the near infrared region.

An important use for the compounds of this invention resides in their incorporation into pressure- or heat-sensitive record systems as a colorable reactant for development of color on application of a mark-forming force. Hence, it is an object of this invention to provide substances having near infrared color response and chromogenic properties, which substances can be incorporated in a web or coated onto the surface of a web to provide a record sheet or a manifolding unit, and which are useful in carrying out methods of marking involving a reactive contact with a color-activating material to develop dark-colored materials in areas where marking is desired.

It is an object of this invention to provide improved compounds, based upon the aforementioned fluorene compounds, which are substantially colorless, or slightly colored, offering a variety of chromogenic characteristics, and developing dark-colored substances absorbing at visible and infrared wavelengths upon contact with color-activating materials.

The fluroene compounds of this invention represented by the general formula (1) are novel and in themselves substantially colorless crystals showing no absorption in the near infrared region, but when in contact with color-developing agents such as, for example, Japanese acid clay, phenol-formaldehyde polymers, hydroxybenzoic acid, bisphenol A, etc. they form a blue to green color, and the resulting color-formed image shows not only marked absorption in the near infrared region but also excellent light fastness. Thus, the fluorene compounds of this invention represented by the general formula (1) are possessed of excellent properties as the chromogenic material.

Compounds of this invention having an interesting utility are those of the formula:

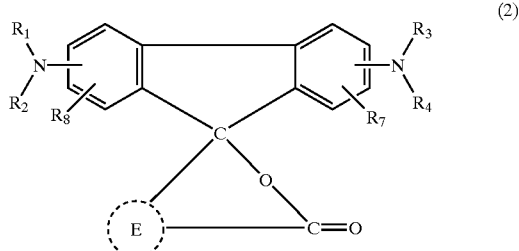

(2)

wherein
E is:

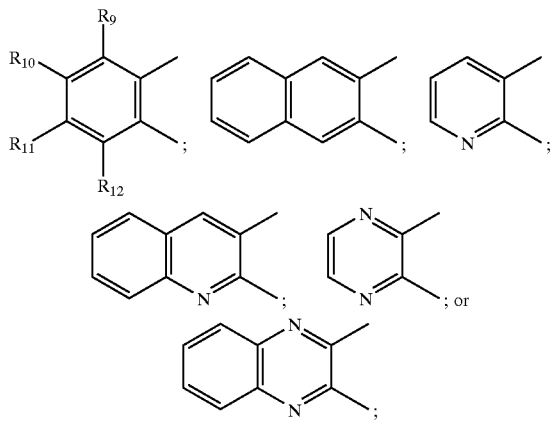

$R_9$, $R_{10}$, $R_{11}$ and $R_{12}$ are: hydrogen, halogen or

each of $R_1$, $R_2$, $R_3$, $R_4$, $R_5$ and $R_6$ is independently hydrogen, alkyl of not more than 12 carbon atoms which is unsubstituted or substituted by halogen, hydroxyl, cyano or lower alkoxy or is cycloalkyl, phenyl, benzyl, or phenyl or benzyl which is substituted by halogen, lower alkyl or lower alkoxy or $R_1$ and $R_2$ or $R_3$ and $R_4$ or $R_5$ and $R_6$ together with the nitrogen atom to which they are attached is a 5- or 6-membered heterocyclic radical selected from the group consisting of pyrrolidino, piperidino; pipecolino, morpholino, thiomorpholino and piperazino; and each of $R_7$ and $R_8$ is independently hydrogen, lower alkyl, lower alkoxy or halo.

Particularly interesting fluorene compounds of this invention are those of the formula:

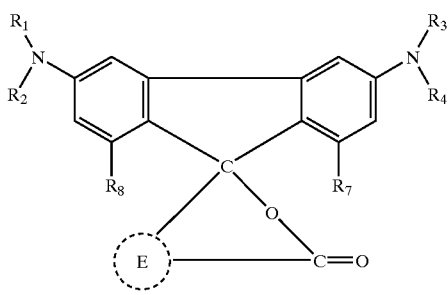

(3)

wherein E represents an optionally substituted benzene, naphthalene, pyridine or pyrazine ring.

Each of $R_1$, $R_2$, $R_3$ and $R_4$ independently represents hydrogen, alkyl of not more than 12 carbon atoms, cyclohexyl, phenyl, benzyl or tolyl or $R_1$ and $R_2$ or $R_3$ and $R_4$ together with the nitrogen atom to which they are attached represent pyrrolidino, piperidino, pipecolino, morpholino, thiomorpholino or piperazino.

$R_7$ and $R_8$ are as previously defined.

The preferred fluorene compounds of this invention are those of the formula:

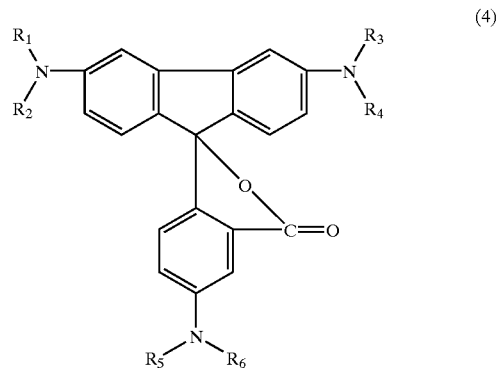

(4)

wherein each of $R_1$, $R_2$, $R_3$, $R_4$, $R_5$ and $R_6$ independently represents hydrogen, alkyl of not more than 12 carbon atoms, cyclohexyl, phenyl, benzyl or tolyl or $R_1$ and $R_2$ or $R_3$ and $R_4$ or $R_5$ and $R_6$ together with the nitrogen atom to which they are attached represent pyrrolidino, piperidino, pipecolino, morpholino, thiomorpholino or piperazino.

Especially preferred fluorene compounds of the formula (4) are those wherein each of $R_1$, $R_2$, $R_3$, $R_4$, $R_5$ and $R_6$ independently represents alkyl of not more than four carbon atoms.

This invention also relates to a process for the manufacture of the fluorene compounds represented by formulas (1), (2), (3) and (4) which comprises subjecting the compound represented by the following general formula to diazotization followed by ring closure:

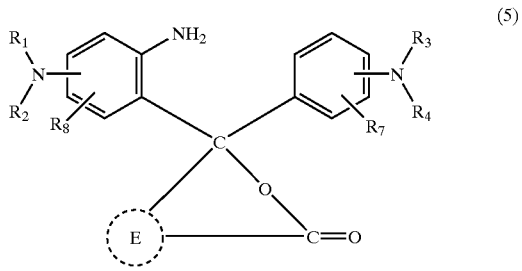

(5)

wherein E, $R_1$, $R_2$, $R_3$, $R_4$, $R_7$, and $R_8$ are as previously defined.

The chromogenic compounds of this invention are eligible for use in pressure-sensitive and thermally-sensitive mark-forming systems. Pressure-sensitive mark-forming systems provide a marking system of disposing on and/or within sheet support material unreacted mark-forming components and a liquid solvent in which one or both of the mark-forming components is soluble, said liquid solvent being present in such form that it is maintained isolated by a pressure-rupturable barrier from at least one of the mark-forming components until application of pressure causes a breach of the barrier in the area delineated by the pressure pattern. The mark-forming components are thereby brought into reactive contact, producing a distinctive mark.

The pressure-rupturable barrier, which maintains the mark-forming components in isolation preferably comprises microcapsules containing liquid solvent solution. The microencapsultion process utilized can be chosen from the many known in the art. Well known methods are disclosed in U.S. Pat. Nos. 2,800,457; 3,041,289; 3,533,958; 3,755,190; 4,001,140 and 4,100,103. Any of these and other methods are suitable for encapsulationg the liquid solvent containing the chromogenic compounds of this invention.

The method of marking comprises providing a chromogenic compound of the present invention and bringing such chromogenic compound into reactive contact, in areas where marking is desired, with an acidic color-activating substance to produce a colored form of the chromogenic compound.

The acidic materials can be any compound within the definition of a Lewis acid, i.e. an electron acceptor. These materials include clay substances such as attapulgite, bentonite and montmorillonite and treated clays such as silton clay as disclosed in U.S. Pat. Nos. 3,622,364 and 3,753,761, materials such as silica gel, talc, feldspar, magnesium trisilicate, pyrophyllite, zinc sulfate, zinc sulfide, calcium sulfate, calcium citrate, calcium phosphate, calcium sulfate, calcium citrate, calcium phosphate, calcium fluoride and barium sulfate, aromatic carboxylic acids such as salicylic acid, derivatives of aromatic carboxylic acids and metal salts thereof as disclosed in U.S. Pat. No. 4,022,936 and acidic polymeric materials such as phenol-formaldehyde polymers, phenol-acetylene polymers, maleic acid-rosin resins, partially or wholly hydrolyzed styrene-maleic anhydride copolymers and ethylene-maleic anhydride copolymers, carboxy poly-methylene and wholly or partially hydrolyzed vinyl methol ether maleic anhydride copolymers and mixtures thereof as disclosed in U.S. Pat. No. 3,672,935.

The fluorene compounds of this invention can be synthesized as follows. The compound represented by the general formula (5) is diazotized in sulfuric acid at about −5 to about 10° C., and then the reaction is allowed to proceed at a temperature of about 10 to about 100° C. for several hours to complete ring closure. In addition, the yield can be more effectively improved by carrying out the ring closure in the presence of either elemental copper in powder form or a copper compound. Next, the reaction product is neutralized with an alkali and the deposit thus formed is purified with solvent by the conventional method, whereby the fluorene compound is obtained as substantially colorless crystals.

The following examples are given merely as illustrative of the present invention and are not to be considered as limiting. All parts and percentages throughout the application are by weight, unless specified otherwise.

Some examples of the fluorene compound of this invention, referring to structure (4) on page 6, are listed in Table 1, together with their respective melting points.

TABLE 1

| Ex. No. | $R_1$ | $R_2$ | $R_3$ | $R_4$ | $R_5$ | $R_6$ | Melting Point (° C.) |
|---|---|---|---|---|---|---|---|
| 1 | —$CH_3$ | —$CH_3$ | —$CH_3$ | —$CH_3$ | —$CH_3$ | —$CH_3$ | 244–246 |
| 2 | —$C_2H_5$ | —$C_2H_5$ | —$CH_3$ | —$CH_3$ | —$CH_3$ | —$CH_3$ | 235–238 |
| 3 | —$C_2H_5$ | —$C_2H_5$ | —$C_2H_5$ | —$C_2H_5$ | —$CH_3$ | —$CH_3$ | 188–191 |
| 4 | —$C_4H_9$ | —$C_4H_9$ | —$CH_3$ | —$CH_3$ | —$CH_3$ | —$CH_3$ | 150–152 |
| 5 | —$C_4H_9$ | —$C_4H_9$ | —$C_2H_5$ | $C_2H_5$ | —$CH_3$ | —$CH_3$ | 139–141 |
| 6 | —$CH_3$ | —$CH_3$ | —$CH_3$ | —$CH_3$ | —$C_2H_5$ | —$C_2H_5$ | 244–246 |
| 7 | —$C_2H_5$ | —$C_2H_5$ | —$CH_3$ | —$CH_3$ | —$C_2H_5$ | —$C_2H_5$ | 164–166 |
| 8 | —$C_4H_9$ | —$C_4H_9$ | —$CH_3$ | —$CH_3$ | —$C_2H_5$ | —$C_2H_5$ | 128–131 |
| 9 | —$C_2H_5$ | —$C_2H_5$ | —$C_2H_5$ | —$C_2H_5$ | —$C_2H_5$ | —$C_2H_5$ | 210–211 |
| 10 | —$C_4H_9$ | —$C_4H_9$ | —$C_2H_5$ | —$C_2H_5$ | —$C_2H_5$ | —$C_2H_5$ | 148–150 |
| 11 | —$CH_3$ | —$CH_3$ | —$CH_3$ | $CH_3$ | —$C_4H_9$ | —$C_4H_9$ | 197–198 |
| 12 | —$C_2H_5$ | —$C_2H_5$ | —$CH_3$ | —$CH_3$ | —$C_4H_9$ | —$C_4H_9$ | 177–178 |
| 13 | —$CH_3$ | —$CH_3$ | 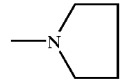 * | | —$CH_3$ | —$CH_3$ | 278.5–279.5 |
| 14 | —$CH_3$ | —$CH_3$ | 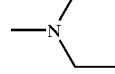 * | | —$CH_3$ | —$CH_3$ | 229.5–231 |
| 15 | —$CH_3$ | —$CH_3$ | 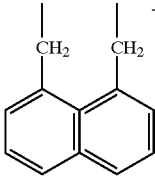 | | —$CH_3$ | —$CH_3$ | 238–240 |

*$R_3$ and $R_4$ together with the nitrogen atom to which they are attached.

EXAMPLE 1

8.6 parts of 3-(2-amino-4-dimethylaminophenyl)-3-(4-dimethylaminophenyl)-6-dimethylaminophthalide were dissolved in a mixture of 37 parts of concentrated sulfuric acid and 12 parts of water and cooled to 0° C. A solution prepared by dissolving 1.4 parts of sodium nitrite in 37 parts of concentrated sulfuric acid was added dropwise to the above described solution over a period of about 30 min. at 0–5° C., and at that temperature reaction was allowed to proceed for 2 hours so as to complete azotization. Next, after the addition of 0.2 g of copper powder, the temperature of the reaction liquid was slowly elevated to 80° C. and stirring was continued for about 20 hours at 80–90° C. to complete ring closure. The reaction product was cooled, poured into 500 parts of ice water and made alkaline with 20% sodium hydroxide. The deposit formed was filtered off and purified with a solvent such as toluene, etc. by the conventional method, whereby the fluorene compound of Example 1 was obtained as white crystals. Yield 7.2 parts (87.2%), m.p. 244–246° C.

By elemental analysis it was confirmed that the compound of Example 1 has the molecular formula $C_{26}H_{27}N_3O_2$.

|  | C | H | N |
| --- | --- | --- | --- |
| Calcd. | 75.51 | 6.59 | 10.16 |
| Found | 75.39 | 6.61 | 10.00 |

Compounds of Examples 2–15 in Table 1 were prepared, using appropriate starting materials, in procedures similar to that for the synthesis of Example 1.

EXAMPLE 16

Preparation of Heat-Sensitive Copy Paper 4 parts of the fluorene compound of Example 1 were ground along with 10 parts of 10% aqueous solution of polyvinyl alcohol and 6 parts of water to give a dispersion (referred to as Component A). Separately to this, 4 parts of bisphenol A were also ground along with 10 parts of 10% aqueous solution of polyvinyl alcohol and 6 parts of water to give a dispersion (referred to as Component B).

1 part of Component A and 6 parts of Component B were mixed, and the resulting mixture was applied to a support and dried to give heat-sensitive recording paper. The heat-sensitive recording paper thus obtained forms a green color when applying heat by means of a heat pen or the like. The color image formed in this way has excellent light-fastness as well as marked absorption in the near infrared region.

EXAMPLE 17

Preparation of Pressure-Sensitive Copy Paper

The fluorene compound of Example 1 is dissolved in a solvent such as alkylnaphthalene, or the like, and sealed into capsules by the conventional method. These capsules are coated onto the undersurface of a support, and dried to give an upper sheet (CB sheet). On the other hand, a solid acid such as phenol compounds, etc. is coated onto the uppersurface of a support to give a lower sheet (CF sheet). When the upper sheet and the lower sheet superposed in such a manner that both the coated surfaces can face each other are pressed by writing with a pen, etc. a bluish-green copied image is formed on the lower sheet. This copied image is fairly light-fast showing absorption in the near infrared region.

The invention being thus described, it will be obvious that the same may be varied in many ways. Such variations are not to be regarded as a departure from the spirit and scope of the invention and all such modifications are intended to be included within the scope of the following claims.

What is claimed is:

1. A record system comprising a support web and a compound represented by the formula:

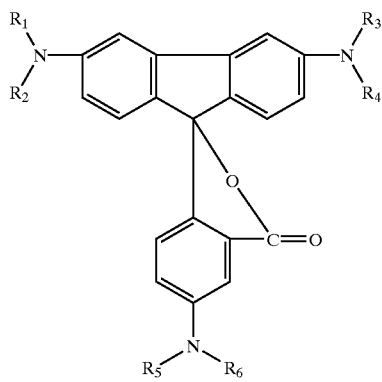

wherein each of $R_1$, $R_2$, $R_3$, $R_4$, $R_5$ and $R_6$ independently represents hydrogen, alkyl of not more than 12 carbon atoms, cyclohexyl, phenyl, benzyl or tolyl or $R_1$ and $R_2$ or $R_3$ and $R_4$ or $R_5$ and $R_6$ together with the nitrogen atom to which they are attached represent pyrrolidino, piperidino, pipecolino, morpholino, thiomorpholino or piperazino.

2. The record system of claim 1 wherein each of $R_1$, $R_2$, $R_3$, $R_4$, $R_5$ and $R_6$ independently represents alkyl of not more than four carbon atoms.

3. The record system of claim 2 wherein $R_1$, $R_2$, $R_3$, $R_4$, $R_5$ and $R_6$ represent methyl.

4. The record system of claim 1, 2 or 3 in which the system is heat-sensitive.

5. The record system of claim 1, 2 or 3 in which the system is pressure-sensitive.

6. A record system comprising a support web and a compound represented by the formula:

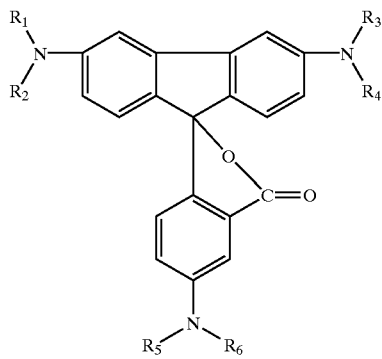

wherein each of $R_1$, $R_2$, $R_3$, $R_4$, $R_5$ and $R_6$ represent ethyl.

7. The record system of claim 6 in which the system is heat-sensitive.

8. The record system of claim 6 in which the system is pressure-sensitive.

9. A record system comprising a support web and a compound represented by the formula:

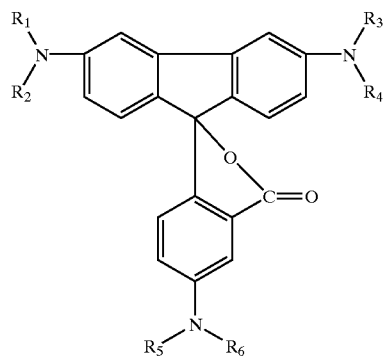

wherein $R_1$ and $R_2$ or $R_3$ and $R_4$ or $R_5$ and $R_6$ together with the nitrogen atom to which they are attached represent pyrrolidino, piperidino or morpholino.

10. The record system of claim 9 in which the system is heat-sensitive.

11. The record system of claim 9 in which the system is pressure-sensitive.

* * * * *